United States Patent
Singh et al.

(10) Patent No.: US 6,570,389 B2
(45) Date of Patent: May 27, 2003

(54) PREVENTION OF ARCING IN POWER SUPPLIES

(75) Inventors: Prabjit Singh, Poughkeepsie, NY (US); George T. Galyon, Fishkill, NY (US); Lenas J. Hedlund, Pine Island, MN (US); Steven Mazzuca, New Paltz, NY (US); Victor A. Ronken, Rochester, MN (US); Yiping Yao, Lagrangeville, NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 09/881,996

(22) Filed: Jun. 15, 2001

(65) Prior Publication Data

US 2002/0190722 A1 Dec. 19, 2002

(51) Int. Cl.$^7$ ................................................. G01N 27/62
(52) U.S. Cl. ....................................................... 324/459
(58) Field of Search ............................ 324/459; 218/150

(56) References Cited

U.S. PATENT DOCUMENTS 4,521,653 A * 6/1985 Yoshiyasu .................... 218/150

OTHER PUBLICATIONS

"Comparision of Arc Tracking Tests in Various Aerospace Environments" T Stereber, A Hammoud D. McCall, Conf. Record of 1996 IEEE International Symposium on Electrical Insulation 1996 vol. 1 pp. 349–352.

"Computer Animated Digital Arc Diagnostic System" by A Shea D. Boles, Y. Chien & R. Zeigler Electrical Contacts 1993—Proceedings of 39$^{th}$ IEEE Holm Conf on Electrical Contacts, 1993 pp. 237–243.

* cited by examiner

Primary Examiner—Christine Oda
(74) Attorney, Agent, or Firm—Floyd A. Gonzalez; James E. Murray

(57) ABSTRACT

A power supply to be tested is placed in a vacuum chamber; the power supply is turned on and gas pressure in the chamber is reduced. As the gas pressure is reduced below 1 atmosphere, the breakdown voltage decreases; when the breakdown voltage decreases to the value of the applied voltage, arcing occurs as long as the applied voltage is greater than a minima. When a site arcs, the site is noted; the power supply is removed from the vacuum chamber; the arc site is conformally coated and the coated cured. Thereafter, the power supply is returned to the vacuum chamber and the test process repeated until the power supply no longer arcs. Thus the partial pressure test can identify the sites that have a possibility of arcing in the field and the design of the power supply modified by use of one or more conformal coatings or by otherwise changing the configuration of the power supply.

11 Claims, 3 Drawing Sheets

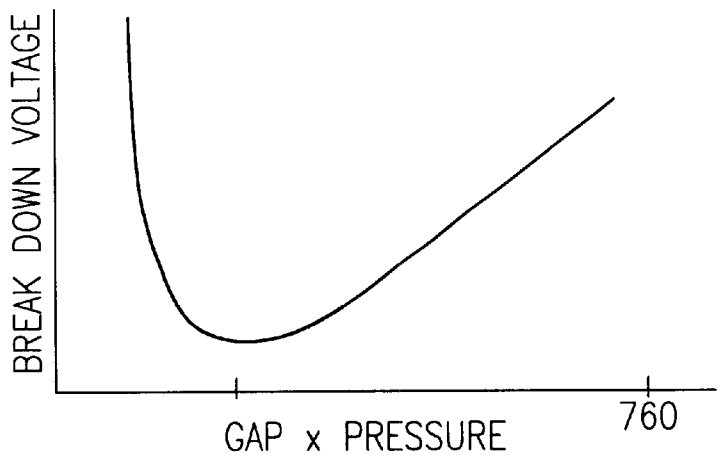
FIG.4
Prior Art
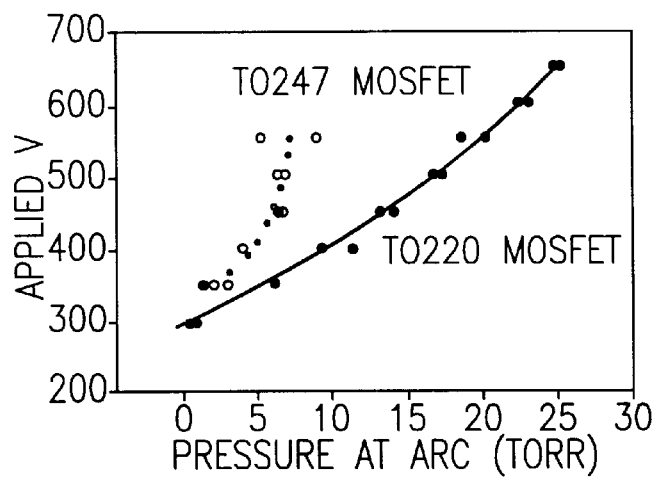
FIG.5
| SOLDER PADS GAP | ARC VOLTAGE WITHOUT ZINC WHISKERS | ARC VOLTAGE WITH ZINC WHISKERS |
|---|---|---|
| 0.5MM | ~3000 V | ~1800 V |
| 1.0MM | ~4000 V | NO ARC UP TO 5000 V |
| 1.5MM | NO ARC UP TO 5000 V | NO ARC UP TO 5000 V |
FIG.6

PREVENTION OF ARCING IN POWER SUPPLIES

FIELD OF THE INVENTION

The present invention relates to power supplies and more particularly, to the testing, design and fabrication of power supplies so as to prevent arcing.

BACKGROUND OF THE INVENTION

Arcing is increasingly becoming a serious power supply failure mode mainly because of the ever increasing density of power supply circuitry, achieved by narrower feature spacings and increasing switching frequencies resulting from pressure on power supply designers to keep up with the ever shrinking logic circuitry. Arcing occurs when air gaps with high electric fields becomes electrically conductive (see F. Llewellyn-Jones, "Ionization and Breakdown in Gases", John Wiley and Sons, Inc, 1957). Free electrons present in air, due to natural radioactivity and cosmic events, accelerate under the influence of electric field towards the positively charged feature (anode). At high enough velocities, these free electrons gain enough energy to produce ionizing collisions with air molecules. Each ionizing collision produces an ion and an additional electron that in turn accelerates and causes additional ionizing collisions resulting in electron avalanche. The first effect of this high concentration of primary electrons and ions is a sudden drop in voltage accompanied by glow discharge. Next, the enhanced concentration of electrons, and thus ions, due to the secondary (thermionic and field) emission of electrons from the negatively charged surface (cathode) results in a sharp increase in current and drop in voltage, to a near zero value, across the gap. The secondary emission of electrons from the cathode is the result of positive ions striking the cathode.

In static electric fields, electrons are removed when they reach the anode and are lost to the ionization process. But, if the electric field is periodically reversed, because of switching waveforms, the direction of electron motion will also be periodically reversed. The electrons thus have lesser chance of being lost to the anode, spending more time in the plasma and causing more ionizing collisions and build up of electron and ion concentrations. The electron and ion concentrations can build up to high enough concentrations to cause arcing with less need for the secondary electron emission from the cathode to replace the primary electrons lost to the node. High frequency, thus, aids the avalanche process leading to arcing at lower electric fields.

Ionization and breakdown in gases has been the subject of intense research by physicists, the early work being carried out by J. J. Thomson and J. S. Townsend at the Cavendish Laboratory, Cambridge, U.K. However, the somewhat irreproducible nature of arcing in electronic hardware has discouraged a thorough and comprehensive undertaking by the engineering profession to map out the conditions necessary for arcing in computer power supplies. Generally, an arc damage in field returned power supplies is readily visible to the unaided eye. But in some supplies that fail in the field due to arcing, the damage is to limited in size so as to be invisible to the unaided eye. A possible reason for the limited arc damage is that a fast solid-state circuit breaker extinguishes the arc before it can do any damage to the power supply. As a result, a power supply that trips its fast circuit breaker in the field, due to arcing, may be diagnosed by a failure analysis laboratory as having no defect. It takes painstaking examination of such field failures to identify arcing as the root cause of these failures. There are two relevant papers on this subject. One paper deals with burn down prevention in static power converter equipment (Luderook and M. Ehsani, "Burndown Prevention in Static Power Converter Equipment:, IEEE Industry Applications Magazine, March/April 1995, pgs. 46–53); and, the other is a military standard for testing power supplies for high altitude applications (MIL-STO-810E, Environmental Testing Methods and Engineering Guidelines, Method 500.3, "Low Pressure Altitudes" Sections 11, Jul. 14, 1989).

Therefore it is an object of the present invention to predict the propensity of power supplies to arc in the field.

It is a further object of the present invention to build power supplies with a reduced propensity to arc.

BRIEF DESCRIPTION OF THE INVENTION

In accordance with the present invention, the power supply to be tested is placed in a vacuum chamber; the power supply is turned on and gas pressure in the chamber is reduced while a camcorder photographs the power supply. As the gas pressure is reduced below 1 atmosphere, the breakdown voltage decreases; when the breakdown voltage decreases to the value of the applied voltage, arcing occurs as long as the applied voltage is greater than a minima. When a site arcs, the site is noted; the power supply is removed from the vacuum chamber; the arc site is conformally coated and the coating cured. Thereafter, the power supply is returned to the vacuum chamber and the test process repeated until the power supply no longer arcs or arcs below a safe pressure considered safe. Thus the partial pressure test can identify the sites that have a possibility of arcing in the field and the design of the power supply modified by use of one or more conformal coatings or by otherwise changing the configuration of the power supply.

BRIEF DESCRIPTION OF THE DRAWINGS

The present invention can best be understood by reading the accompanying detailed description of an embodiment thereof while referring to the accompanying figures of which:

FIG. 4 is a plot of breakdown voltage as a function of air pressure;

FIG. 5 is a plot of arc pressure for particular MOSFETs as a function of drain-to-source DC voltage;

FIG. 6 is a table illustrating arcing at pure DC voltages.

DETAILED DESCRIPTION OF THE INVENTION

Figure 1:
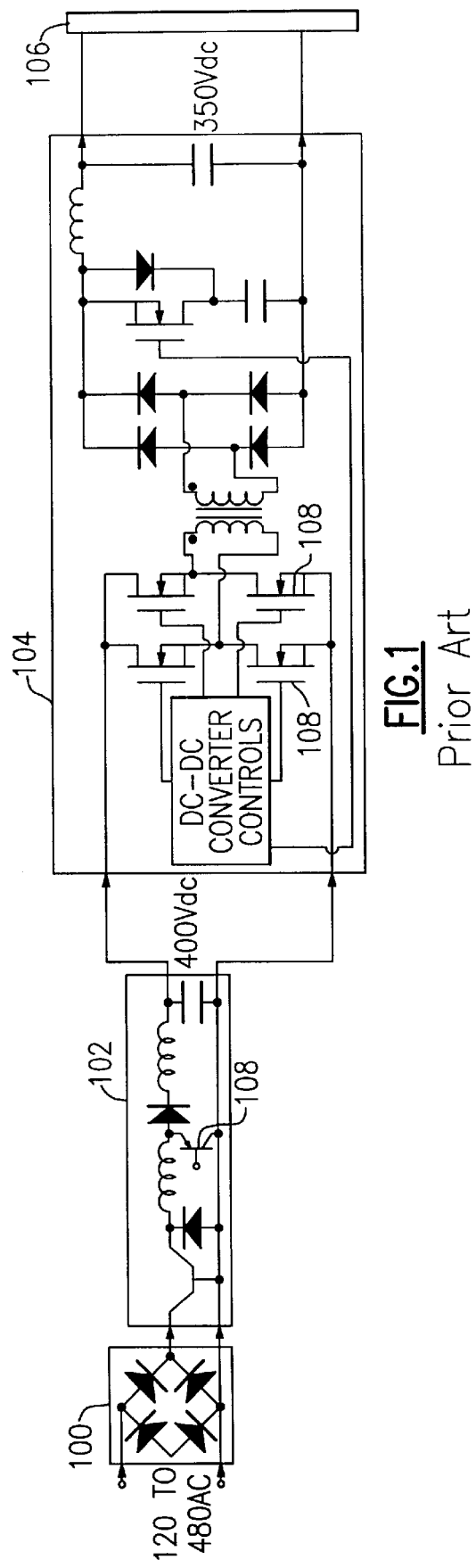
FIG. 1 is a schematic diagram of a switching mode power supply system.

As shown in FIG. 1, a switching mode power supply system, used to power a large computer, typically includes a rectifier 100 and power factor corrected rectifier 102 followed by a dc—dc converter 104 that provides the intermediate bus voltage to downstream point-of-load dc—dc converters. The power factor corrected converter usually consists of a boost converter which raises the full-wave rectified ac line voltage to greater than the peak amplitude of the ac line voltage. This relatively high dc output voltage (350–700V) of the boost rectifier is transformed by a dc—dc converter 104 to the desired intermediate bus voltage provided to a mother board 106 of a computer. The MOSFETs of the rectifier and the downstream dc—dc converters switch this high voltage (350–700V) at frequencies in the range of 50–300 kHz. Higher switching frequency is used to make the reactive parts of the power supplies more compact.

We have found that arcing occurs in power supplies in the field when the following three conditions are present: (1) switching waveforms with large amplitudes and high frequency harmonics; (2) narrow gaps between the features across which the harmonics with large amplitudes and high frequencies appear; and (3) physical contamination, such as airborne zinc whiskers or some other metallic debris that can deposit in the narrow gaps. Zinc whiskers originate from zinc electroplating located on the under side of raised floor tiles which are commonly used in computer rooms. Other sources of metallic debris may be the result of any hardware assembly operations or nearby construction activity.

Figure 2:
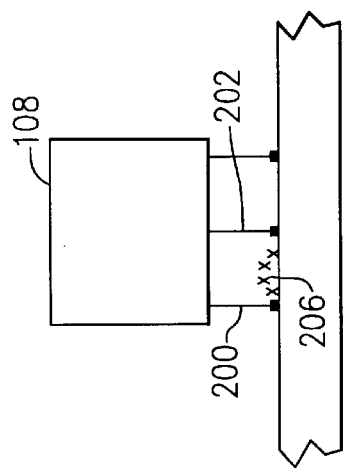
FIG. 2 is a schematic diagram of a MOSFET in the power supply system of FIG. 1.

Visual inspection of arced power supplies showed that arcing occurred most often across features associated with the drain-to-source connections of the MOSFETs 108 particularly in the dc to dc converters 104. In an attempt to identify the contamination causing the arcing, surface chemical analysis of a few arc traces was done. In a few cases, time of flight secondary ion mass spectrometry surface analysis of the arc trace between the drain and source terminals 200 and 202 of the MOSFET, shown in FIG. 2, revealed the distinct presence of zinc from zinc whiskers 206 causing an arc in a power supply. The presence of zinc in this arc trace was also confirmed using Auger analysis.

Generally, an arc damage in field returned power supplies is readily visible to the unaided eye. But in some supplies that fail in the field due to arcing, the damage is too limited in size to be visible to the unaided eye. A possible The reason for the limited arc damage is that a fast solid-state circuit breaker extinguishes the arc before it can do any damage to the power supply. As a result, a power supply that trips its fast circuit breaker in the field, due to arcing, may be diagnosed by a failure analysis laboratory as having no defect. It takes painstaking examination of such field failure to identify arcing as the root cause of these failures.

In accordance with the present invention, the arcing phenomenon was reproduced in the laboratory using a partial vacuum test.

Figure 3:
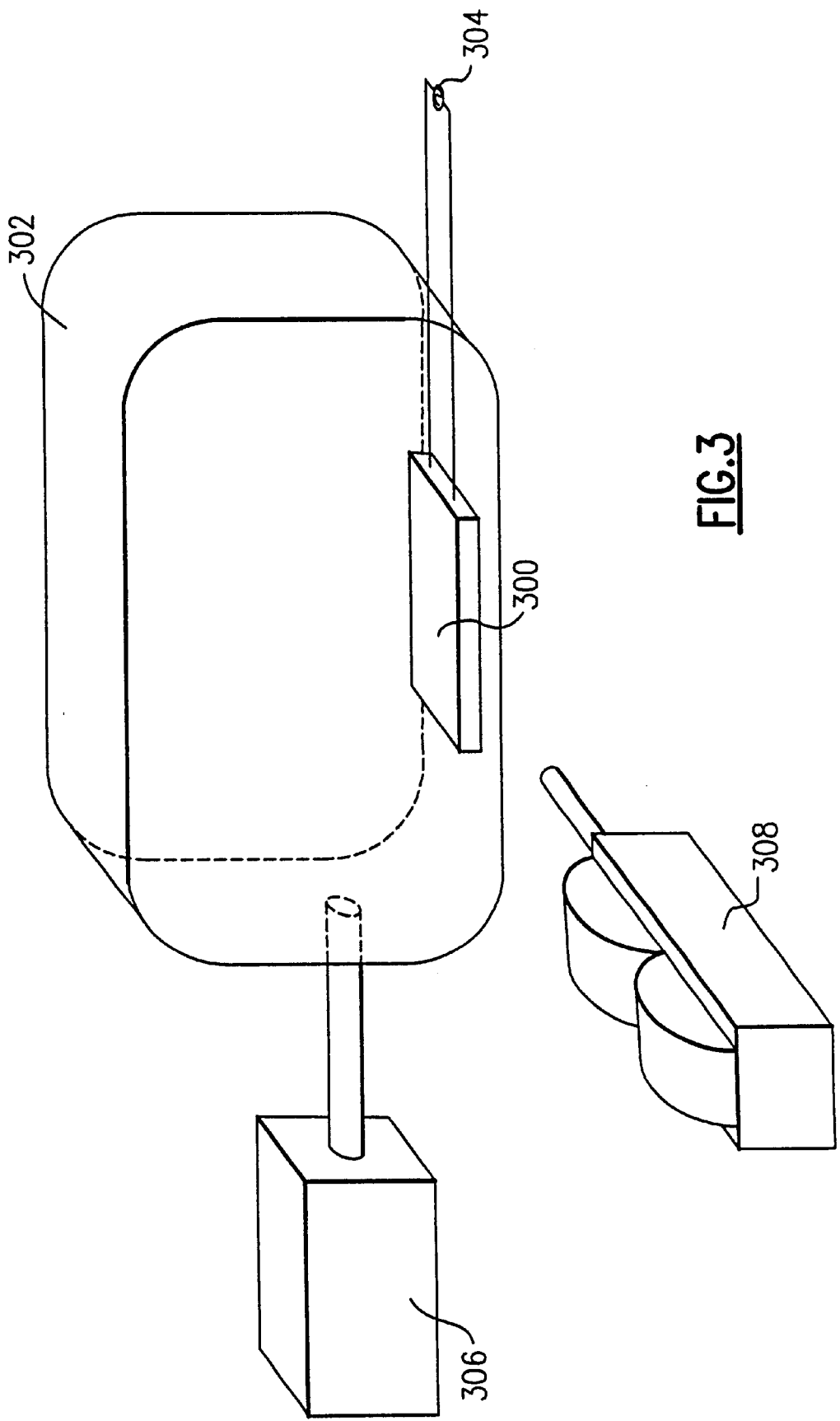
FIG. 3 is a schematic diagram of a vacuum chamber set up for testing the power supply of FIG. 1.

As shown in FIG. 3, power supply 300 under test is installed in a vacuum chamber 302 and powered up using an AC power source. The vacuum chamber is then pumped down with a vacuum pump 306. The partial vacuum test procedure proceeds as follows:

1. The power supply under test 300 is placed in a vacuum chamber and then powered up from the AC power source 304.
2. The vacuum pump 306 is turned on to evacuate the air from the chamber. When the pressure in the chamber drops below 100 Torr, the rate of air should be lowered to about 10 Torr/minute.
3. When the pressure drops below about 25 Torr a high speed (120 frames/second) video camera 308 is turned on to capture any arcing event.
4. If no arcing occurs and the pressure has dropped well below 1 Torr, the pressure is raised and lowered slowly (10 Torr/minute) three times, between about 1 Torr and about 20 Torr. If an arc occurs, note the pressure and proceed to the next step. If no arc occurs, the power supply is in a state in which it will probably not arc in the field, and the test is completed. If the power supply arcs below a safe pressure, it too is in a state in which it will probably not arc in the field, and the test is complete.
5. An arced power supply should be removed from the chamber and the arc location noted and compared to the picture captured on the video. The video may capture more arcing events than the arc damaged sites on the power supply, because some arcs may be too weak to leave damage traces on the power supply.
6. If the power supply that arced is still functional, it can be used for the next test run. If the damage can be repaired, it should be done so; if not, a new power supply should be used for the next test run.
7. On the new, repaired or undamaged power supply from the previous run, coat any region that arced in the previous run (runs) with a room temperature vulcanizing (RTV) coating such as Humiseal 1C59 conformal coating after thoroughly cleaning the region with isopropyl alcohol. Let the conformal coating cure overnight.
8. Insert the power supply in the vacuum chamber and repeat steps 1–6, until the power supply arcs no more, or arcs below a pressure considered safe.
9. Catalog all the sites that arced along with the pressures at which the arcing occurred.
10. Coating the cataloged areas of other power supplies of the same design with the conformal coating.

If arcing does not occur, or occurs below a safe pressure, in vacuum with repeated up and down cycling of pressure between about 1 and 20 Torr, then that power supply should not arc in the field.

The partial vacuum test conforms to Paschen's law, that relates the breakdown voltage to the arithmetic product of gas pressure and the gap across which the voltage is applied. As shown in FIG. 4, for a given gap, the breakdown voltage decreases as the gas pressure is decreased. At lower gas pressures the mean-free path of the electrons increases giving them more time to gain kinetic energy and hence increase the probability of ionizing collisions. Paschen's law curve has a minimum below which decreasing pressure reduces the density of gas molecules to such an extent that the probability of ionizing collisions is now dominated not by the mean-free path, which is now very long, but by the probability that a high velocity electron will strike an air molecule. Breakdown voltage is also a function of the switching waveform frequency and the ringing frequency of the power supply and the amount of conductive contamination present in the power supply environment. The partial vacuum test aggravates the arcing situation by reducing the breakdown voltage by lowering the gas pressure. The location on the power supply where the breakdown voltage is the lowest is the first to arc in the partial vacuum test and in the field. Since the drain-to-source leads and solder pads and other associated features of the converter power train MOSFETs have high voltages with high switching frequencies, the tendency is for the arcing to be associated with these MOSFETs. The signature of arcing in the field is similar to that found in the partial vacuum test.

One can infer from Paschen's law that as the pressure is decreased, more and more sites with lower electric fields will arc. In order for the partial vacuum test to correctly predict the field arcing propensity of a power supply, we must know what range or arc pressures translates into a high acing propensity in the field. To determine this arc pressure range, we subjected half a dozen power supplies with different topologies and power ratings to a battery of partial vacuum tests. the results were similar for all the power supplies. We discussed the test results of one of these power supply designs known to have a high field arcing propensity in a paper entitled "Predicting Arcing in Power Supplies" published in the APEC-2001 Proceeding, pgs. 225 to 229 (the contents of the publication are hereby incorporated by reference). The sequence of test results showed the general trend that as the regions, where the arc is known to occur in the field, are coated with RTV (room temperature vulcanizing) silicone sealant, the pressure at which arcing occurs decreases. The power supply design discussed arced at about 13 Torr pressure in the flyback converter region when no RTV silicone sealant was applied. Coating the features that arced caused arcing at somewhat lower pressure across another pair of features within the flyback region. Coating this second pair of features caused arcing at still lower pressure across a third pair of features within the flyback region. Fully coating the flyback region, reduced the arc pressure to less than about 3 Torr. This trend of decreasing arc pressure with increasing degree of protection against arcing by coating agreed with Paschen's law and was observed on all the power supply designs tested. From this observation, it can be inferred that the lower the pressure at which a power supply arcs, the more rugged it is from an arcing point of view.

The arc pressure pass/fail criterion was found to depend on the input dc voltage to the dc—dc converters. Generally speaking, we have found that dc voltage by itself does not cause arcing in power supplies. Therefore, the arc pressure, associated with features across which there is essentially pure dc voltage, should be considered in the safe range. FIG. 5 shows a plot of applied drain-to-source dc voltage, across $TO_{220}$ and TO247 MOSFETs, and the pressure at which arcing occurred. The gates or MOSFETs were shorted to the sources to ensure that the MOSFETs stayed off. Knowing that dc voltages do not cause arcing in power supplies in the field, the arc pressures of FIG. 5 should be considered safe. For example, if there is a TO220 MOSFET in the switching network of a dc—dc converter with 500 V dc input, arc pressure of about 16 Torr should be considered in the safe range; whereas, in the same power supply, the safe arc pressure for a TO247 MOSFET should be about 7 Torr. Arc pressures range associated with arcing in the field should begin at some pressure above the safe value determined by the dc experiments of FIG. 5.

In order to be able to design arc-free power supplies, we had to determine the minimum allowable spacing between features across which high voltages with high switching harmonics appear. For this arc-proof spacing determination, we used the zinc whisker spray test method along with specially prepared circuit board coupons with 1-mm radius solder pads with gaps ranging from 0.5 mm to 8 mm. The drain-to-source voltage from the power train MOSFET of one of the six power supplies under test was applied to the electrodes. Zinc whiskers were sprayed between the electrodes in a somewhat controlled manner. The results showed that arcing occurred across gaps as wide as 2.75 mm. Arcing did not occur across 3 mm and wider gaps. Based on this study, we concluded that features subjected to 350 V switching at 200 kHz should be separated by at least 3 mm. If the spacing is less than 3 mm, these features should be coated with RTV silicone sealant to prevent arcing in the field.

To show that a dc voltage by itself does not cause arcing, even in the presence of conductive contamination, zinc whisker spray coupon experiments were done with pure dc voltage across the electrode gaps. FIG. 6 summarizes the findings. In the absence of conductive contamination such as zinc whiskers, arcing across a 0.5 mm gap requires about 3000 Vdc. Presence of zinc whiskers in the gap, reduces the arc voltage to about 1800 V. These voltages are well above the 350–700 V present in power supplies. The reason for the reduced breakdown voltage in power supplies, therefore, has to be due to the presence of contamination and due to high frequency switching and ringing of the MOSFET drain-to-source voltage. Note that in FIG. 6, row 3, the lower value of arc voltage in the presence of zinc whiskers compared to that in the absence of zinc whiskers, illustrates the somewhat irreproducible nature of the arcing phenomenon.

Above we have described one method of improving the resistance of power supplies to arcing. It will be apparent to those skilled in the art that various modifications may be made in this method without departing from the invention. Therefore it should be understood that the present invention is not limited to the above embodiment but includes those embodiments that do not depart from the spirit and scope of the appended claims.

What we claim is:

1. A method of fabricating a power supply comprising:
    testing at least one power supply below its operating atmospheric pressure in a pressure range to increase the probability of ionizing collisions;
    checking for arcing at various pressures in the testing range; and
    modifying the power supply configuration to minimize the pressure at which the supply arcs.

2. The method of claim 1, wherein said modifying includes:
    applying a conformal coating to at least one arc site found by the testing and checking in fabricating other power supplies.

3. The method of fabricating power supplies of claim 2, wherein the testing at below atmospheric pressure includes a plurality of testing cycles including at least one cycle which occurs after said conformal coating has been applied to at least one arc site identified in a previous test cycle.

4. The method of claim 1 including providing a separate testing of MOSFETs used in the power supply where a contaminant is applied to the terminals of the MOSFETs to select minimum terminal spacing.

5. The method of claim 4, wherein the contaminant is zinc whiskers sprayed at electrode gaps of MOSFETs in the power supply.

6. The method of claim 3, wherein at least one testing cycle includes evacuating a chamber containing a lowered power supply to below 12 Torr/minute when the pressure in the chamber is below 100 Torr.

7. The method of claim 6, wherein at least one of the testing cycles where no arcing has occurred after the pressure has dropped below 1 Torr includes raising and lowering the pressure slowly a plurality of times.

8. The method of claim 7 including repeating the raising and lowering of the pressure at least 3 times.

9. The method of claim 8, wherein the raising and lowering of the pressure occurs at lower than 10 Torr/minute.

10. The method of claim 9, wherein the raising of the pressure is between 1 Torr and 20 Torr.

11. The method of claim 9 includes;
    using a high speed camera to monitor the testing; and
    comparing the camera results with visually detected arc sites.

* * * * *